US008974737B2

(12) United States Patent
Erickson

(10) Patent No.: US 8,974,737 B2
(45) Date of Patent: Mar. 10, 2015

(54) SPACE DISINFECTION

(71) Applicant: Saban Ventures PTY Limited, Alexandria (AU)

(72) Inventor: Gary Erickson, Alexandria (AU)

(73) Assignee: Saban Ventures Pty Limited, Alexandria (AU)

( * ) Notice: Subject to any disclaimer, the term of this patent is extended or adjusted under 35 U.S.C. 154(b) by 0 days.

(21) Appl. No.: 13/868,168

(22) Filed: Apr. 23, 2013

(65) Prior Publication Data

US 2014/0023558 A1    Jan. 23, 2014

Related U.S. Application Data

(63) Continuation of application No. 11/997,878, filed as application No. PCT/AU2006/001115 on Aug. 4, 2006, now Pat. No. 8,444,919.

(30) Foreign Application Priority Data

| Aug. 4, 2005 | (AU) | ................................ | 2005904181 |
| Aug. 4, 2005 | (AU) | ................................ | 2005904196 |
| Aug. 4, 2005 | (AU) | ................................ | 2005904198 |
| Feb. 15, 2006 | (AU) | ................................ | 2006900748 |

(51) Int. Cl.
   *A61L 2/16* (2006.01)
   *A01N 59/00* (2006.01)
   (Continued)

(52) U.S. Cl.
   CPC ................ *A01N 59/00* (2013.01); *A01N 25/06* (2013.01); *A61L 2/06* (2013.01); *A61L 2/208* (2013.01);
   (Continued)

(58) Field of Classification Search
   CPC ......... A61L 9/00; A61L 9/14; A61L 2202/00; A61L 2202/10; A61L 2202/11; A61L 2202/15; A61L 2209/00; A61L 2209/10; A61L 2209/13; A61L 2209/131; A61L 2209/132

USPC .......................................... 422/120, 123–125
See application file for complete search history.

(56) References Cited

U.S. PATENT DOCUMENTS

| 3,476,506 A | 11/1969 | Andersen et al. |
| 3,481,689 A | 12/1969 | Rosdahl et al. |

(Continued)

FOREIGN PATENT DOCUMENTS

| EP | 0679407 A2 | 11/1995 |
| GB | 663720 | 12/1951 |

(Continued)

OTHER PUBLICATIONS

International Search Report, PCT/AU2006/001115, dated Sep. 1, 2006, 4 pages.

(Continued)

*Primary Examiner* — Sean E Conley
(74) *Attorney, Agent, or Firm* — Senniger Powers LLP

(57) ABSTRACT

A method for disinfecting a volume or surfaces bounding a volume comprising nebulizing a solution comprising a sterilizing agent in a solvent having a lower boiling point than the sterilizing agent, for example ultrasonic nebulization of aqueous hydrogen peroxide, to form a nebulant. The nebulant is subjected to energy of a kind and for a duration sufficient to vaporize solvent in preference to sterilizing agent, eg heating element means, infra red, laser, microwave, RF or other radiation generating means; induction heating means; heat exchanger means; conduction means; convection means; or mechanical energy transfer means to increase the concentration of the agent in the nebulant particles. Vaporized solvent is removed from the gas stream at or above atmospheric pressure and, if necessary, the nebulant is cooled to below 70° C. The volume or surfaces are exposed to the nebulant for a time sufficient to sterilize said volume or surfaces. Also, apparatus for carrying out the method.

21 Claims, 4 Drawing Sheets

(51) Int. Cl.
*A01N 25/06* (2006.01)
*A61L 2/06* (2006.01)
*A61L 2/20* (2006.01)
*A61L 2/22* (2006.01)
*A61L 2/24* (2006.01)
*C01B 15/013* (2006.01)

(52) U.S. Cl.
CPC ... *A61L 2/22* (2013.01); *A61L 2/24* (2013.01); *C01B 15/013* (2013.01); *A61L 2/16* (2013.01); *A61L 2/20* (2013.01); *A61L 2202/24* (2013.01)
USPC ............ 422/128; 422/120; 422/123; 422/125

(56) References Cited

U.S. PATENT DOCUMENTS

| | | | |
|---|---|---|---|
| 3,950,247 A | 4/1976 | Chiang et al. | |
| 4,022,324 A | 5/1977 | Schuster | |
| 4,191,543 A | 3/1980 | Peters | |
| 4,296,068 A | 10/1981 | Hoshino | |
| 4,366,125 A | 12/1982 | Kodera et al. | |
| 4,680,163 A | 7/1987 | Blidschun et al. | |
| 4,718,985 A | 1/1988 | Kjellander | |
| 4,744,951 A | 5/1988 | Cummings et al. | |
| 4,958,529 A | 9/1990 | Vestal | |
| 4,978,430 A | 12/1990 | Nakagawa et al. | |
| 5,454,274 A | 10/1995 | Zhu | |
| 5,611,842 A | 3/1997 | Friesen | |
| 5,843,209 A | 12/1998 | Ray et al. | |
| 5,851,485 A | 12/1998 | Lin et al. | |
| 6,066,294 A | 5/2000 | Lin et al. | |
| 6,325,972 B1 | 12/2001 | Jacobs et al. | |
| 6,379,616 B1 | 4/2002 | Sheiman | |
| 6,500,465 B1 | 12/2002 | Ronlan | |
| 6,656,426 B1 | 12/2003 | Wang et al. | |
| 6,977,061 B2 | 12/2005 | Lin et al. | |
| 7,014,813 B1 | 3/2006 | Watling et al. | |
| 7,122,166 B2 | 10/2006 | Parrish | |
| 2002/0119075 A1 | 8/2002 | Jacobs et al. | |
| 2003/0143110 A1 | 7/2003 | Kritzler et al. | |
| 2003/0183576 A1 | 10/2003 | Ohara et al. | |
| 2003/0192799 A1 | 10/2003 | Addy et al. | |
| 2004/0005240 A1 | 1/2004 | Adiga et al. | |
| 2004/0022673 A1 | 2/2004 | Protic | |
| 2004/0062692 A1 | 4/2004 | Lin et al. | |
| 2005/0252856 A1 | 11/2005 | Parrish | |

FOREIGN PATENT DOCUMENTS

| | | |
|---|---|---|
| GB | 2346095 A | 8/2000 |
| JP | 55-137007 | 10/1980 |
| JP | 60-206408 | 10/1985 |
| JP | 63-175602 | 7/1988 |
| JP | 02-273518 | 11/1990 |
| JP | 10-284458 | 10/1998 |
| JP | 2003-095617 | 4/2003 |
| JP | 2003-180802 | 7/2003 |
| JP | 2004-267755 | 9/2004 |
| WO | 9111374 A2 | 8/1991 |
| WO | 9966961 A1 | 12/1999 |
| WO | 0121223 A1 | 3/2001 |
| WO | 02056988 A2 | 7/2002 |

OTHER PUBLICATIONS

International Preliminary Report on Patentability, PCT/AU2006/001115, dated Jul. 30, 2007, 3 pages.

"Content and Format of Premarket Notification [510(k)] Submissions for Liquid Chemical Sterilants/High Level Disinfectants," Jan. 3, 2000, Guidance for Industry and FDA Reviewers, CDRH, 59 pages.

McDonnell, G., et al., "Antiseptics and Disinfectants: Activity, Action, and Resistance," 1999, Clin Microbiol Rev, 12/1:147-179.

Japanese Utility Model Patent Application 54-105847, Published as S56-024977, 2000, 12 pages.

FIGURE 3

- Process return-flow in
- Micro nebulant Out-flow
- Splash Guard
- Hydrogen peroxide Aqueous Mixture
- Water bath
- Gel-filled transmission membrane
- Connection to Transducer driver PCB
- 2.4 MHz Piezo Electric Transducer

SPACE DISINFECTION

REFERENCE TO CORRESPONDING APPLICATIONS

The present application is a continuation of U.S. application Ser. No. 11/997,878 which is a U.S. National Stage Application of International Application No. PCT PCT/AU2006/001115, filed Aug. 4, 2006, and is now U.S. Pat. No. 8,444,919, and claims priority to Australian Patent Application No. 2006900748, filed Feb. 15, 2006, and Australian Patent Application Nos. 2005904181, 2005904196, and 2005904198 all filed on Aug. 4, 2005.

FIELD OF THE INVENTION

The present invention relates to a method and apparatus for disinfecting or decontaminating large exposed surfaces or spaces which may be infected with bacteria, fungi, viruses, or fungal or bacterial spores.

A space to be disinfected may be a chamber, for example, a shipping container, a hospital operating theatre or hospital ward, an aircraft interior, or may be a shopping mall, subway system, warehouse, silo, or other enclosed or semi-enclosed space. Exposed surfaces may be exemplified by surfaces of walls or partitions defining the space, or work surfaces, machinery surfaces, air conditioning ducts, or other surfaces which are interior or can be enclosed or partly enclosed, at least temporarily, for the present purpose.

BACKGROUND OF THE INVENTION

Any discussion of the prior art throughout the specification should in no way be considered as an admission that such prior art is widely known or forms part of common general knowledge in the field.

The most commonly used method for disinfecting such large spaces and surfaces involves the use of gases such as ozone or chlorine dioxide which are oxidative or corrosive and toxic, or may involve gases such as ethylene oxide or aldehydes, such as glutaraldehyde or formaldehyde, which are extremely toxic and which leave potentially harmful residues on surfaces. Steam is sometimes used and is hazardous to the operator because of the high temperatures involved and leaves a dense moisture on the surface which may lead to rusting.

From a health and environmental perspective it would be preferable to use hydrogen peroxide or peracetic acid as a disinfectant. Hitherto, as discussed in Ronlan U.S. Pat. No. 6,500,465, high density fine aerosols (aerosol droplet diameter less than 50 microns) of peracetic acid or hydrogen peroxide suitable for disinfecting have only been considered stable at 100% relative humidity.

Also hitherto, aerosols have suffered from the general problems that they were not effective at penetrating covered surfaces. This meant that door locks, hinges and the like as well as occluded surfaces such as, for example, an area of floor beneath a chair, could harbour organisms.

Another problem is that aerosol particles tend to settle and wet out the surfaces on which they fall, leaving an undesirable residue on the surface which must be cleaned off. In our co-pending Australian Patent Applications 2005904196, filed Aug. 4, 2005, entitled, "Improved Aerosol" and 2006900748, filed Feb. 15, 2006, entitled, "Membrane Sterilization" the content of which is incorporated by reference, sterilising or disinfecting agents are disclosed which can be adapted for treating large surfaces or spaces.

OBJECT OF THE INVENTION

Its an object of this invention to provide a method for disinfecting a large area or disinfecting a volume and which avoids or ameliorates at least some of the disadvantages of the prior art. It is a further object of the invention to provide improved apparatus and improved fumigants for carrying out the method.

By disinfecting a volume is meant that the air in the volume and organisms if any suspended in the air are disinfected.

It is an object of preferred embodiments to be able to disinfect surfaces in chambers such as operating theatres, wards of hospitals, cold rooms, refrigerators, vans, sea containers, factory areas where disinfection is a requirement and preferably to do so by means which are scalable.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

BRIEF STATEMENT OF INVENTION

According to a first aspect the present invention provides a method for disinfecting an area or a volume comprising the steps of:
(1) nebulising a solution comprising a sterilizing agent in a solvent to form a nebulant of finely divided particles of the solution in a gas stream, said solution including a solvent having a lower boiling point than the sterilizing agent;
(2) subjecting the nebulant to energy of a kind and for a duration sufficient to vaporize solvent in preference to sterilizing agent, whereby to increase the concentration of the agent in the nebulant particles;
(3) removing solvent vaporized in step 2 from the gas stream at or above atmospheric pressure and, if necessary, cooling the nebulant to below 70° C.; and
(4) exposing said surface to nebulant from step 3 for a time sufficient to disinfect said area or volume.

In preferred embodiments the nebulant is a solution of hydrogen peroxide in water, desirably at an initial concentration of 35% or less. If desired the method can sterilize said surface, or the surfaces containing said volume According to a second aspect the invention provides a method for disinfecting a large area or volume comprising the steps of:
(1) exposing said surface to, or introducing to said volume, a nebulant comprising a solution of hydrogen peroxide in water; and
(2) controlling the relative humidity in the volume or in the vicinity of said surface to from 20% to 70% RH.

The invention will now be more particularly described by way of example only with reference to the accompanying drawings.

BRIEF DESCRIPTION OF THE DRAWING

FIG. 3 shows a schematic for a nebuliser for use in accordance with embodiments of the invention.

DETAILED DESCRIPTION

Figure 1:
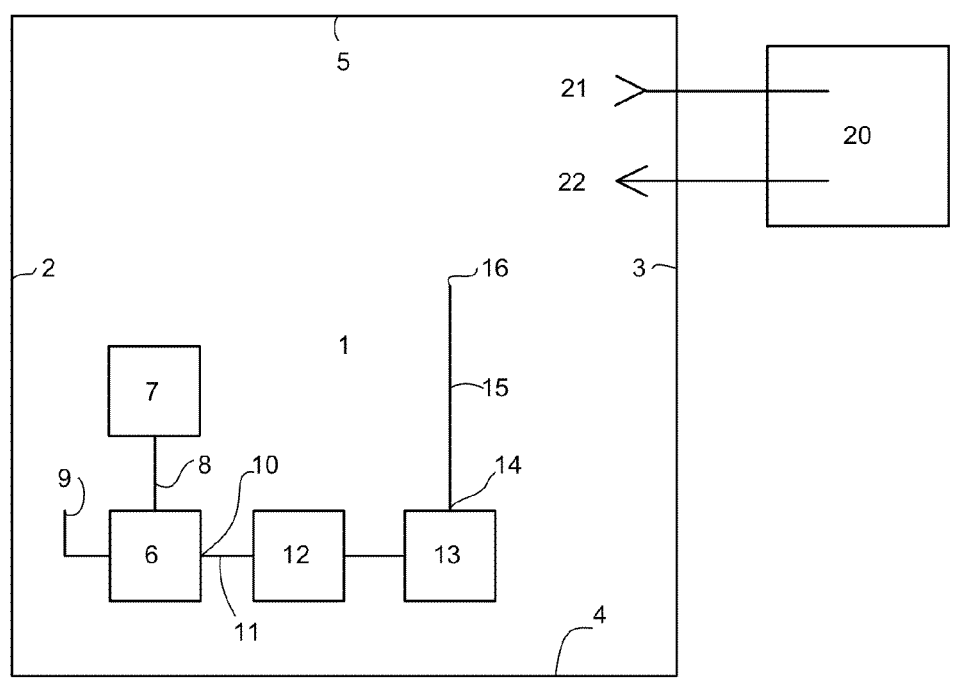
FIG. 1 shows a schematic of a space disinfection apparatus in accordance with an embodiment of the invention.
Figure 2:
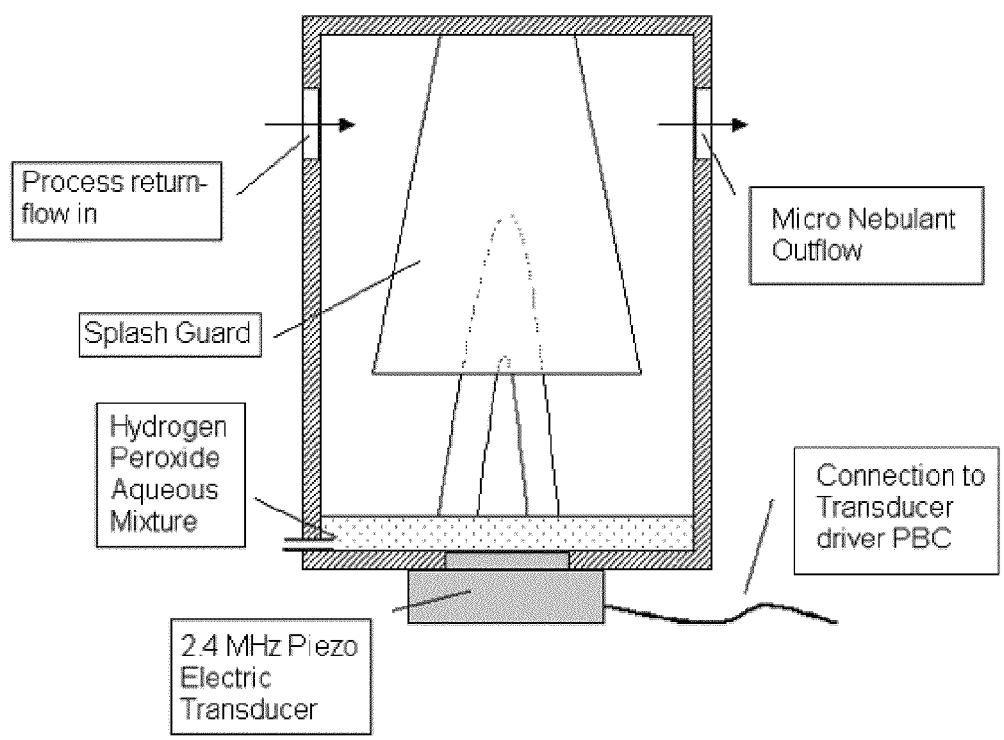
FIG. 2 shows a schematic for a nebuliser for use in accordance with embodiments of the invention.
Figure 4:
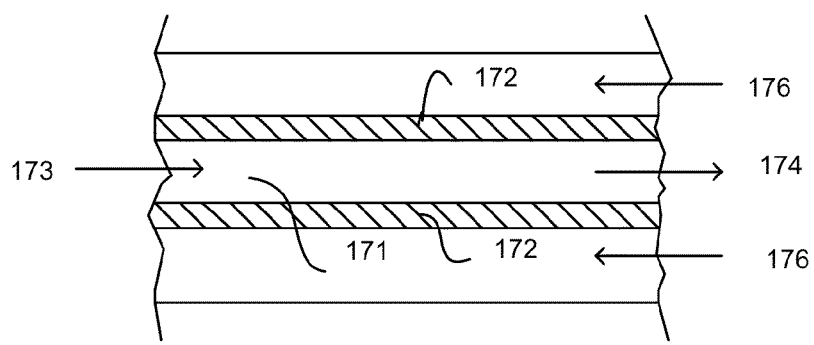
FIG. 4. shows a schematic of a membrane concentrator for use in accordance with embodiments of the invention.

With reference to FIG. 1 there is shown schematically a first embodiment of the invention. In FIG. 1 there is shown in vertical cross-section a chamber 1 to be disinfected. Chamber 1 is defined is by walls 2, 3, floor 4, and ceiling 5 (the remaining walls and entry not being illustrated. Within the chamber is an ultrasonic nebuliser 6 for example of the kind described in our copending application "Improved Aerosol" at FIGS. 3 and 4, which are shown here as FIGS. 2 and 3. Nebuliser 6 is fed in this example with a 35% solution of hydrogen peroxide in water contained in a reservoir 7 via feed line 8. Nebuliser 6 draws air at air inlet 9, in this example from within Chamber 1. The nebulant generated by nebuliser 6 exits at nebulant outlet 10 and is drawn via a conduit 11 on the suction side of fan 12 and pumped from the pressure side of fan 12 to a heater 13. Nebulant from nebuliser 6 passes over a heater element in heater 13 and is directed from heater outlet 14 via conduit 15 to a disperser 16 from where it permeates the chamber volume. Moisture removal unit 20 draws air from within chamber 1 at 21, cools and dehumidifies it and returns it to the room at a predetermined temperature and relative humidity. In the present example moisture removal unit 20 is an air conditioning system.

In operation nebuliser 6 nebulises a solution comprising hydrogen peroxide in water from reservoir 7 to form a nebulant of finely divided particles of the solution in the air stream. The water has a lower boiling point than the hydrogen peroxide In this example the nebulant is heated in heater 13 sufficiently to vaporize water in preference to peroxide, whereby to increase the concentration of the peroxide in the nebulant particles to around 60-70% and reducing the particle size as discussed in our co-pending applications.

Disperser 16 may be one or more baffles, which may be stationary or driven or may be other means such as a fan for dispersing the nebulant. In this embodiment of the invention the water vapour removed from the nebulant during passage through heater 13 is removed from chamber 1 by air-conditioning system 20 at or above atmospheric pressure which draws nebulant and water vapour from the room removes water vapour and returns cooled nebulant into the space.

The treated nebulant consists of particles having a smaller size (nano particles) than untreated particles produced by the nebuliser (micro particles) and therefore having a much lesser tenancy to settle out of the gas stream. The smaller particles also have a much greater rate of diffusion and ability to penetrate into covered spaces. The treated nebulant has a much higher concentration than the untreated nebulant or feed solution. In our co pending application "Improved Aerosol", nebulant from the nebuliser was heated in a heat exchanger and then cooled in a condenser to remove water (with reference to FIG. 2 of that application, vapour from nebuliser 5 is heated in 17 and then cooled in 20 to remove water). In the present FIG. 1, by controlling the relative humidity within space 1 by air conditioner 20 a similar effect is obtained as was obtained in the examples of our co pending specification.

As described in more detail in our co pending applications:
  Other sterilizing agents may be used and the sterilizing agent may be dissolved in other solvents,
  Other kinds of nebuliser may be used
  Other gases may be fed to the nebuliser
  Solutions of hydrogen peroxide solution in air are highly preferred.
  The solvent may be removed in preference to the biocide by supplying energy in other ways
  Water may be removed from the chamber by other means
  It is desirable to control the relative humidity, and temperature within predetermined limits as therein detailed.

In the present application the air conditioning may take the form of a ducted room system or may be a portable unit placed in the room. The unit need not employ a condenser but may be for example a desiccator system such as a twin cycle system which absorbs moisture during one cycle, and is then dried venting the moisture externally during a second cycle while a twin unit absorbs moisture, or a device such as disclosed in our copending "Membrane Concentrator" application, for example, a device shown in FIG. 4 in which a current of nebulant enters conduit 171 at 173 and exits at 174 and countercurrent of air or another dry gas 176 pass on either side of a semipermeable membrane 172. The nebulant droplets exiting at 174 are more concentrated than when they enter at 173.

A catalytic destructor may be employed to remove excess peroxide from the chamber. The reservoir, nebuliser, fan, and heater may be combined in a portable unit which can be moved from chamber to chamber, and if desired a separate air drying or air conditioning system may be made portable for use in the same chamber as the nebuliser or may be combined with the nebuliser unit.

A preferred embodiment will now be described by way of example In this embodiment 35% hydrogen peroxide in water was used as the biocide. The components of the device included a nebuliser array, (6×2 cm diameter transducers in a circular array), a heater element, a first and second fan and a dehumidifier system. The dehumidifier used had been a small air conditioning unit positioned appropriately within the space. The purpose of the first fan was to propel nanoparticles from the heater into the space and the purpose of the second fan was to ensure an equal distribution of the aerosol to all surfaces within the space.

It was found to be highly desirable that the transducers are synchronized within the array otherwise the waveforms produced will potentially cancel each other out within the liquid resulting in an inefficient production of peroxide nebulant to the heater.

Example 1

Tests were conducted in an 8 cubic meter volume of cubic shape.

Samples were coated with an inoculum at levels of approximately log 6 and air dried for 2 hours on the plastic petri dish (Techno-Plas, Australia) in a laminar flow cabinet. The samples were placed in various positions in the room including on the walls, floor and ceiling. In the example below the samples were placed in the centre of the wall adjacent to the corner and on the floor approximately in the centre of the room and were exposed to hydrogen peroxide nebulant treated as described with reference to FIG. 1.

Unless otherwise stated, the operating conditions were:
Solution: 35% peroxide
Temp: 25 degrees
RH: fluctuated 45% to ~65%. Sometimes 75%
Nebulizer array 2.4 MHz
Peroxide vapour: 300-500 ppm
Air flow post heater: 400-600 cubic meters per hour.
Heater Temp: 80-90 degrees
Peroxide delivery: Optimally approximately 0.75 gram per cubic meter per minute, ie 12.6 grams for the 8 cubic meter room.

The results obtained for various bacteria was as follows:
(In the tables "TNTC"=too numerous to count, "ND"=not done)

Table 1 shows the results for an experiment in which open carriers were used.

Table 2 shows the result for the same conditions except that the carriers were in closed petri dishes, i.e. dishes with lids. Closed Petri dishes allow penetration across very narrow gaps. The dishes and lids are specifically designed to allow gas exchange with an incubator environment while keeping the dish free from external microbial contamination.

Table 3 and Table 4 show the results for *Aspergillus niger*.

Example 2

The test of example 1 was repeated in a 69 cu m. chamber under substantially the same conditions except as shown in table 5

Table 5 shows the scalability of the process to a 69 cubic meter room.

In general, results with *Bacillus stearothermophillus* showed that greater than 6 log reductions could be obtained at 550 ppm on both the walls and floor.

Example 3

Air was recirculated through a catalytic destructor system (employing in this example a mixture of metal oxides including aluminium oxide) to "decontaminate" the room by removal of excess peroxide. Otherwise the peroxide can be more slowly broken down by recirculating the conditioned dry air within the space or possibly by increasing the temperature to help facilitate the process. It took approximately one hour to reduce the peroxide vapour levels to about 10 ppm from a maximum of approximately 400-700 ppm in a 16 cubic meter room. The final 10 ppm took much longer to reduce to a significant degree.

To an extent which is obvious from the disclosure herein contained, features disclosed in this specification may be combined with features or combinations of features disclosed in our co pending applications and such combinations are within the scope of the invention herein disclosed.

TABLE 1

| Species | Room size | Peroxide vapour level (ppm) | Contact time (min) | Floor (log reduction) | Wall (log reduction) |
|---|---|---|---|---|---|
| *Pseudomonas aeruginosa* (open carriers) | 8 cubic meters | | | | |
| | | 50 | 2.5 | TNTC | 3.5 |
| | | | 5 | TNTC | 3.6 |
| | | | 10 | TNTC | 4.3 |
| | | | 20 | ND | ND |
| | | 200 | 2.5 | 4.4 | 5.7 |
| | | | 5 | 5.2 | 5.7 |
| | | | 10 | 3.4 | 5.7 |
| | | | 20 | 5.7 | 5.7 |
| | | 350 | 2.5 | 6.1 | 4.4 |
| | | | 5 | 6.1 | 5.8 |
| | | | 10 | 6.1 | 6.1 |
| | | | 20 | 6.1 | 6.1 |

TABLE 2

| Species | Room size | Peroxide vapour level (ppm) | Contact time (min) | Floor (log reduction) | Wall (log reduction) |
|---|---|---|---|---|---|
| *Pseudomonas aeruginosa* (closed carriers) | 8 cubic meters | | | | |
| | | 300 | 5 | ND | 6.7 |
| | | | 10 | ND | 6.3 |
| | | | 20 | 5.8 | 6.7 |

TABLE 3

| Species | Room size | Peroxide vapour level (ppm) | Contact time (min) | Wall (log reduction) Open carriers | Wall (log reduction) Closed carriers |
|---|---|---|---|---|---|
| *Aspergillus niger* | 8 cubic meters | | | | |
| | | 250 | 5 | 6.3 | 5.1 |
| | | | 10 | 6.3 | 6.3 |
| | | | 20 | 6.3 | 6.3 |
| | | | 30 | 6.3 | 6.3 |
| | | 500 | 5 | 6.9 | 6.9 |
| | | | 10 | 6.9 | 6.9 |
| | | | 20 | 6.9 | 6.9 |
| | | | 30 | 6.9 | 6.9 |

TABLE 4

| Species | Room size | Peroxide vapour level (ppm) | Contact time (min) | Floor (log reduction) Open carriers | Floor (log reduction) Closed carriers | Wall (log reduction) Open carriers | Wall (log reduction) Closed carriers |
|---|---|---|---|---|---|---|---|
| *Aspergillus niger* | 8 cubic meters | 350 | 15 | 6.5 | 6.1 | 5.9 | 5.7 |
| | | 550 | 15 | 6.7 | 6.6 | 6.7 | 6.3 |
| | | | 20 | 7.5 | 7.5 | 7.5 | 7.5 |
| | | | 30 | 7.5 | 7.5 | 7.5 | 6.6 |

TABLE 5

| Species | Room size | Peroxide vapour level (ppm) | Contact time (min) | Location Floor (log reduction) | Location Wall (log reduction) |
|---|---|---|---|---|---|
| *Aspergillus niger* | 69 cubic meters | 500 | | | |
| | | closed | 30 | 6.7 | 6.7 |
| | | open | 30 | 6.7 | 6.7 |

The claims defining the invention are as follows:

1. An apparatus for disinfecting a volume or surfaces bounding a volume comprising:

a nebulizer to produce a nebulant comprising finely divided particles of a solution suspended in a gas, the solution comprising a sterilizing agent and a solvent having a lower boiling point than the sterilizing agent;

means for supplying sufficient energy to the nebulant to selectively vaporize at least some of the solvent to increase the concentration of the sterilizing agent in nebulant particles, wherein the means for supplying sufficient energy to the nebulant to selectively vaporize at least some of the solvent comprises heating element means, infra red, laser, microwave, RF or other radiation generating means; induction heating means; heat exchanger means; conduction means; convection means; or mechanical energy transfer means; and a disperser configured to disperse the nebulant to the volume or surface to be disinfected, the disperser comprising one or more baffles and/or a fan.

2. The apparatus according to claim 1 wherein the disperser comprises a first fan to propel nebulant particles from the means for selectively vaporizing at least some solvent into the volume and a second fan to provide a uniform distribution of the nebulant to surfaces bounding the volume.

3. The apparatus according to claim 1 wherein the means for supplying sufficient energy to the nebulant to selectively vaporize at least some of the solvent comprises a heating element.

4. The apparatus according to claim 1 further comprising means for separating solvent vapor from the gas at atmospheric pressure.

5. The apparatus according to claim 4 wherein the means for separating solvent vapor from the gas comprises a drying agent, a molecular sieve, a membrane, a centrifuge, or a cyclonic separator.

6. The apparatus according to claim 4 wherein the means for separating solvent vapor from the gas at atmospheric pressure is positioned downstream of the disperser.

7. The apparatus according to claim 1 wherein the nebulizer comprises a device selected from the group consisting of ultrasonic nebulizers, sprays, jet nebulizers and piezoelectric nebulizers, operated continuously or cyclically.

8. The apparatus according to claim 1 wherein the disperser comprises a fan configured to disperse the nebulant to the volume or surface to be disinfected.

9. The apparatus according to claim 1 further comprising a fan or pump between the nebulizer and the means for supplying sufficient energy to the nebulant to selectively vaporize at least some of the solvent.

10. The apparatus according to claim 1 further comprising a catalytic destructor for removing sterilizing agent from the volume or surface.

11. A portable apparatus for disinfecting a volume or surfaces bounding a volume comprising:

a nebulizer to produce a nebulant comprising finely divided particles of the sterilizing agent solution suspended in a gas, the solution comprising a sterilizing agent and a solvent having a lower boiling point than the sterilizing agent;

a sterilizing agent feed conduit in fluid communication with the nebulizer;

a heating element configured to supply sufficient energy to the nebulant to selectively vaporize at least some of the solvent to increase the concentration of the sterilizing agent in nebulant particles;

a fan or a pump positioned downstream of the nebulizer and upstream of the heating element to pass the nebulant over the heating element; and a disperser configured to disperse the nebulant to the volume or surface to be disinfected, wherein the disperser is positioned downstream of the heating element and comprises one or more baffles and/or a fan.

12. The apparatus according to claim 11 further comprising means for separating solvent vapor from the gas at atmospheric pressure.

13. The apparatus according to claim 12 wherein the means for separating solvent vapor from the gas comprises a drying agent, a molecular sieve, a membrane, a centrifuge, or a cyclonic separator.

14. The apparatus according to claim 12 wherein the means for separating solvent vapor from the gas comprises an air conditioning system.

15. The apparatus according to claim 11 wherein the means for separating solvent vapor from the gas at atmospheric pressure is positioned downstream of the disperser.

16. The apparatus according to claim 11 further comprising a catalytic destructor for remove sterilizing agent from the volume or surface.

17. The apparatus according to claim 11 wherein the disperser comprises a fan configured to disperse the nebulant to the volume or surface to be disinfected.

18. The apparatus according to claim 11 further comprising a sterilizing agent solution reservoir in fluid communication with the sterilizing agent feed conduit.

19. The apparatus according to claim 11 wherein the nebulizer comprises a device selected from the group consisting of ultrasonic nebulizers, sprays, jet nebulizers and piezoelectric nebulizers, operated continuously or cyclically.

20. The apparatus according to claim 11 wherein the nebulizer comprises an ultrasonic nebulizer.

21. The apparatus according to claim 11 wherein the disperser comprises a first fan to propel nebulant particles from the heater into the volume and a second fan to provide a uniform distribution of the nebulant to surfaces bounding the volume.

* * * * *